United States Patent [19]
Corey et al.

[11] 3,943,151
[45] Mar. 9, 1976

[54] PROSTAGLANDIN INTERMEDIATES

[75] Inventors: Elias J. Corey, Cambridge, Mass.;
Jasjit S. Bindra, Groton; Thomas K. Schaaf, Old Lyme, both of Conn.

[73] Assignee: Pfizer Inc., New York, N.Y.

[22] Filed: Oct. 24, 1973

[21] Appl. No.: 409,068

[52] U.S. Cl. 260/343.2 R; 260/340.9; 260/343.3 R; 260/346.2 R; 260/488 R; 260/488 B; 260/514 D; 260/514 G; 260/586 G; 260/617 F
[51] Int. Cl.² ..................................... C07D 309/30
[58] Field of Search ................. 260/343.5, 343.2 R

[56] References Cited
OTHER PUBLICATIONS
Corey, J.A.C.S. 93, p. 1491, (1971).

*Primary Examiner*—Lorraine A. Weinberger
*Assistant Examiner*—Jane S. Myers
*Attorney, Agent, or Firm*—Connolly and Hutz

[57] ABSTRACT

A new synthesis of key prostaglandin precursors and intermediates employed in their preparation. The novel synthetic sequence of this invention is shorter and more efficient than those previously employed to prepare to key intermediate.

3 Claims, No Drawings

PROSTAGLANDIN INTERMEDIATES

BACKGROUND OF THE INVENTION

This invention relates to a novel synthesis of certain key prostaglandin precursors. In particular, it relates to the synthesis of lactone ester alcohol (8). Several routes already exist for the preparation of this alcohol first described by E. J. Corey in the Journal of American Chemical Society Vol. 93, p 1491 (1971). However all of the existing methods for the preparation of this important intermediate involve many steps which frequently give rise to reduced yields. The sequences of the present invention are short and proceed in high yield and require an inexpensive and readily available starting material.

The prostaglandins are C-20 unsaturated fatty acids which exhibit diverse physiological effects. For instance, the prostaglandins of the E and A series are potent vasodilators (Bergstrom, et al., *Acta Physiol. Scand.* 64:332–33 1965 and Bergstrom, et al., *Life Sci.* 6:449–455, 1967) and lower systemic arterial blood pressure (vasodepression) on intravenous administration (Weeks and King, *Federation Proc.* 23:327, 1964; Bergstrom, et al., 1965, op. cit.; Carlson et al., *Acta Med. Scand.* 183:423–430, 1968; and Carlson, et al., *Acta Physiol. Scand.* 75:161–169, 1969). Another well known physiological action for $PGE_1$ and $PGE_2$ is as a bronchodilator (Cuthbert, *Brit. Med. J.* 4:723–726, 1969).

Still another important physiological role for the natural prostaglandins is in connection with the reproductive cycle. $PGE_2$ is known to possess the ability to induce labor (Karim, et al., *J. Obstet. Gynaec. Brit. Cwlth.* 77:200–210, 1970), to induce therapeutic abortion (Bygdeman, et al., *Contraception*, 4, 293 (1971) and to be useful for control of fertility (Karim, *Contraception*, 3, 173 (1971)). Patents have been obtained for several prostaglandins of the E and F series as inducers of labor in mammals (Belgian Pat. No. 754,158 and West German Pat. No. 2,034,641), and on $PGF_1$, $F_2$, and $F_3$ for control of the reproductive cycle (South African Pat. No. 69/6089). It has been shown that luteolysis can take place as a result of administration of $PGF_2$ [Labhsetwar, Nature 230 528 (1971)] and hence prostaglandins have utility for fertility control by a process in which smooth muscle stimulation is not necessary.

Still other known physiological activities for $PGE_1$ are in the inhibition of gastric acid secretion (Shaw and Ramwell, In: Worcester Symp. on Prostaglandins, New York, Wiley, 1968, p. 55-64) and also on platelet aggregation (Emmons, et al., *Brit. Med. J.* 2:468–472, 1967).

It is now known that such physiological effects will be produced in vivo for only a short period, following the administration of a prostaglandin. A substantial body of evidence indicates that the reason for this rapid cessation of activity is that the natural prostaglandins are quickly and efficiently metabolically deactivated by β-oxidation of the carboxylic acid side-chain and by oxidation of the 15α-hydroxyl group (Anggard, et al., *Acta. Physiol. Scand.* 81, 396 (1971) and references cited therein). It has been shown that placing a 15-alkyl group in the prostaglandins has the effect of increasing the duration of action possibly by preventing the oxidation of the C15-hydroxyl [Yankee and Bundy, JACS 94, 3651 (1972)], Kirton and Forbes, *Prostaglandins*, 1, 319 (1972).

It was, of course, considered desirable to devise new synthetic sequences which would be shorter and more efficient than the previously existing methods. In particular, sequences which required simple starting materials and did not require complex isolation procedures or long and tedious purifications for the various intermediates as do the existing prostaglandin synthesis were sought.

SUMMARY OF THE INVENTION

The present invention comprises a process for the preparation of a compound of the structure:

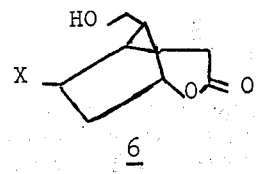

6 wherein X is a halogen, which comprises contacting a halo lactone acid of the structure:

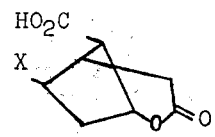

5 with about an equimolar amount of a lower alkyl chlorocarbonate and a trialkyl amine in a reaction-inert solvent at a temperature of from about −20° to 10°C. until reaction is substantially complete and reduction of the mixed anhydride so formed with about one to two equivalents of sodium or zinc borohydride at a temperature of from about −20° to 20°C. until reaction is substantially complete and isolation of product. The invention further embraces the process wherein the above starting halo lactone acid (5) is prepared by a process comprising contacting a halo keto acid of the structure:

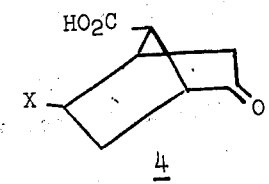

4 with about an equimolar amount of peracetic acid in a reaction inert solvent at a temperature of from about 25°–40° until reaction is substantially complete and isolating the product so produced. Similarly, embraced is the process wherein the above starting halo keto acid (4) is prepared by a process comprising contacting a tricyclene keto acid of the stucture:

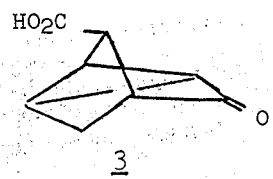

3 with 100–200 times its weight of concentrated hydrochloric acid at a temperature of from about 100°–150°C. until reaction is substantially complete and isolating the product so produced. This invention also includes a process wherein the above starting tricyclene keto acid (3) is prepared by a process comprising contacting a diester of structure:

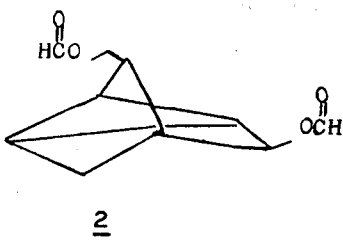

2 with about an equimolar amount of CrO₃ in a reaction inert solvent at a temperature of from about 0°–30°C. until reaction is substantially complete and isolating the product so produced. The instant invention further comprises a process wherein the above starting diester is prepared by a process comprising contacting a compound of structure:

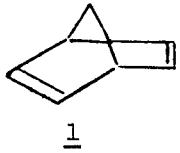

1 with about an equimolar amount of formaldehyde and with 5–10 times its weight of a formic acid in presence of sulphuric acid at a temperature of from about 0°–30°C. until reaction is substantially complete and isolating the product so produced.

Also included in the invention is a process for the preparation of a dilactone of the structure:

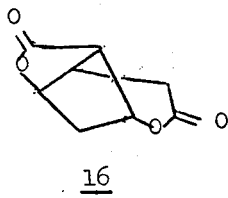

16 which comprises contacting a keto lactone of the structure:

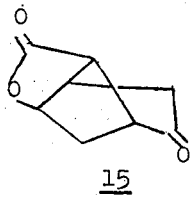

15 with about an equimolar amount of peracetic acid or a perbenzoic acid in a reaction-inert solvent at a temperature of from about 0°–40°C. until reaction is substantially complete and isolation of product. Likewise included in the instant invention is a process wherein the above starting keto lactone (15) is prepared by a process comprising contacting tricyclene keto acid (3) with about fifty times its weight of dilute sulphuric acid at a temperature of from about 100°–175°C. until reaction is substantially complete and isolating the produce so produced. This invention also comprises a process wherein the keto lactone (15) is prepared by a process comprising contacting a ketal lactone of structure:

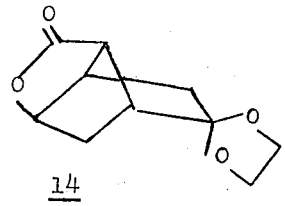

14 with aqueous mineral acid until reaction is substantially complete and isolating the produce so produced. This invention further comprises a process wherein the above starting ketal lactone (14) is prepared by a process comprising contacting a ketal ether of structure:

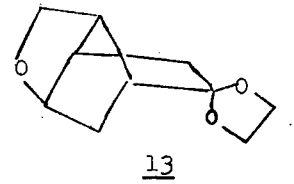

13 with about two times its weight of rutherium tetraoxide in presence of an aqueous alkali metal periodate in a reaction inert solvent until reaction is substantially complete and isolating the product so produced and the process wherein the starting ketal ether (13) is prepared by a process comprising contacting an alcohol ketal of structure:

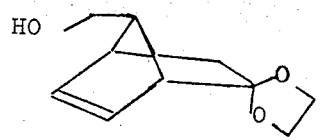

12 with about equimolar amount of mercuric acetate in aqueous tetrahydrofuran until reaction is substantially complete and contacting the organomercurial so formed with a solution of about one equivalent of sodium borohydride in alkali metal hydroxide until reaction is substantially complete and isolating the product so produced. The instant invention further comprises a process wherein the starting alcohol ketal is prepared by a process comprising contacting a keto alcohol of structure:

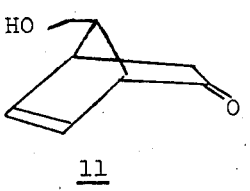

11 with ethylene glycol and a catalytic amount of a strong acid in refluxing reaction inert solvent with azeotropic removal of water produced until reaction is substantially complete and isolating the product so produced and the process wherein the starting keto alcohol (11) is prepared by a process comprising contacting the known compound of structure:

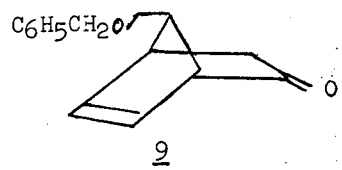

with about one tenth its weight of Boron trifluoride in acetic anhydride at a temperature of from about 0°–20° until reaction is substantially complete and contacting the acetoxy ketone so formed with about one equivalent of aqueous base until reaction is substantially complete and isolation of product.

This invention also comprises novel compounds of the structure:

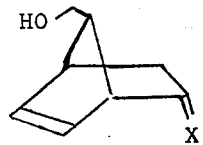

wherein X is oxygen or

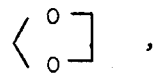

a compound of the structure:

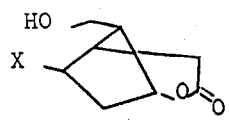

wherein X is chlorine, bromine or iodine; a compound of the structure:

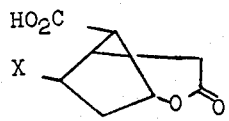

wherein X is chlorine, bromine or iodine; a compound of the structure:

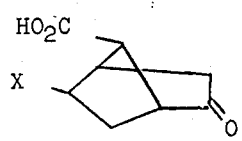

wherein X is chlorine, bromine or iodine; a compound of the structure:

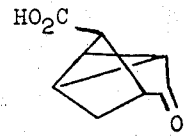

a compound of the structure:

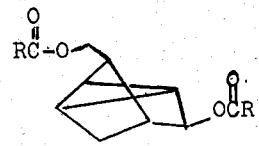

wherein R is hydrogen or lower alkyl, a compound of the structure:

wherein X is oxygen or a compound of the structure:

wherein X is oxygen or and a compound of the structure:

Furthermore, the instant invention also comprises a process wherein the halo lactone 6 is prepared by a process comprising contacting a halo ketone of structure:

with one equivalent of peracetic acid in a reaction inert solvent at a temperature of from about 20°–40°C until reaction is substantially complete and isolating the product so formed and a process wherein the starting halo ketone (27) is prepared by a process comprising contacting a ketone of structure:

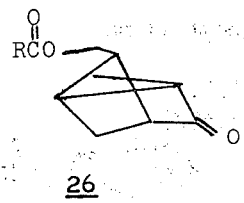

26 wherein R is lower alkyl; with 10–100 times its weight of concentrated hydrochloric acid at a temperature of from about 100°–150° until reaction is substantially complete and isolating the product so formed.

In addition the instant invention comprises a process wherein the tricyclene ketone (26) is prepared by a process comprising contacting a tricyclene alcohol of structure:

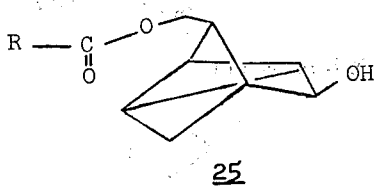

25 wherein R is lower alkyl; with about two equivalents of $CrO_3$ in a reaction inert solvent at a temperature of from about 0°–25° until reaction is substantially complete and isolating the product so formed and a process wherein the starting tricyclene alcohol (25) is prepared by a process comprising contacting a diol of structure:

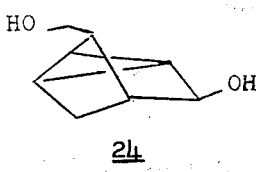

24 with one equivalent of lower alkanoic acid anhydride and a proton acceptor in a reaction inert solvent at a temperature of from about 0°–50°C until reaction is substantially complete and isolating the product so formed.

Also included in the present invention is a process wherein the diol 24 is prepared by a process comprising contacting a compound of the structure:

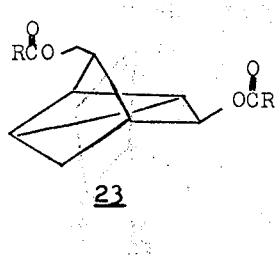

23 wherein R is hydrogen or lower alkyl; with an aqueous solution of an alkali metal hydroxide or carbonate at a temperature of from about 0°–25°C until reaction is substantially complete, a process for the preparation of a lactone of the structure:

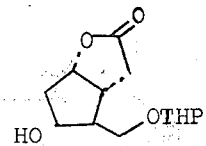

7 which comprises contacting the halo lactone alcohol (6) with an equimolar amount of dihydropyran in presence of a catalytic amount of a strong acid and contacting the resulting ether with an equimolar amount of alkali metal hydroxide and twenty times its weight of 30% hydrogen peroxide in aqueous THF at a temperature of from about —10° to 30°C until reaction is substantially complete and isolation of product and a process wherein the lactone (7) so produced is then treated with about an equimolar amount of p-biphenyl carbonyl chloride in ten times its weight of pyridine until reaction is substantially complete and then treatment with an excess of dilute mineral acid for removal of THP group to produce a compound of the structure:

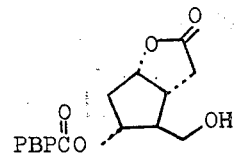

8 and the product isolated.

DETAILED DESCRIPTION OF THE INVENTION

The starting material for the novel synthesis sequences of this invention is norbornadene. This substance is contacted (1 → 2) with formaldehyde or paraformaldehyde in the presence of formic acid with a small amount of mineral acid as a catalyst. It it is desired to produce a diester other than diformate (2) acetic acid or other lower alkanoic acid may be substituted for the formic acid in this reaction. The reaction is conveniently conducted between 0°–30° although high temperatures may be employed if decomposition of the final product is not encountered. Diformate (2) is then oxidized (2 → 3) using Jones' reagent at a reaction temperature of from about 0°–30°. The reaction is conducted in acetone as a solvent optimally at 25°. Keto acid (3) is converted to keto acid (4) wherein X is chlorine by heating (3) in concentrated hydrochloric acid at a temperature of from about 100°–150°. Approximately 100–200 times the weight of keto acid (3) is used. Frequently, a cosolvent such as acetic acid is also employed to increase the solubility of the reactants. If it is desired to produce a keto acid (4) wherein X is Br or I, the hydrochloric acid is replaced by hydrobromic or hydriodic acid respectively. Keto acid (4) is then oxidized (4 → 5) under Bayer-Villiger conditions with peracetic acid, perbenzoic acid, m-chloroperbenzoic acid or m-nitroperbenzoic acid. About one equivalent of this oxidizing agent is used in a reaction inert solvent such as methylene chloride or chloroform. The reaction is carried out conveniently at a temperature of from about 25–40°C. The reaction proceeds more rapidly at the high temperatures. Slightly increased yields may be obtained if the reaction is run in the presence of one equivalent of sodium carbonate or sodium bicarbonate. Lactone acid (5) is then reduced to lactone alcohol (6) by a two-step procedure comprising contacting lactone acid (5) with a lower alkyl halo carbonate in a reaction inert solvent containing an equivalent of an organic base such as triethylamine or triethyldiamine. This reaction is best conducted below room temperature and most conveniently between $-20°$ and $\pm 10°C$ in a reaction inert solvent, typically dimethoxyethane or tetrahydrofuran. The reaction mixture is then contacted with about from 1 to 2 equivalents of sodium borohydride or zinc borohydride in dimethoxyethane and the reaction temperature is maintained from about $-20°$ to $\pm 20°C$. The reaction is temperature held between these limits until reaction is substantially complete. Any reducing agent may be used which does not reduce the lactone ring, however, sodium or zinc borohydride have been found to be most effective. Similarly, for the first step of the conversion (5 → 6) any lower alkyl halo carbonate may be used but ethyl or methyl chlorocarbonate have been found to be most effective.

Halo lactone alcohol (6) is converted to lactone ether (7) by first protecting the alcohol with an acid labile protecting group such as tetrahydropyranyl, 4 methoxypyranyl or trimethylene silyl. This transformation is typically accomplished by treating lactone alcohol (6) with an excess of dihydropyran in the presence of a trace of acid catalyst. P-toluenesulfonic acid is typically employed as a catalyst. After the reaction is substantially complete the excess dihydropyran is removed and the crude ether thus obtained is dissolved in a reaction inert solvent such as tetrahydrofuran or dimethoxyethane and treated with an aqueous lithium hydroxide in the presence of hydrogen peroxide.

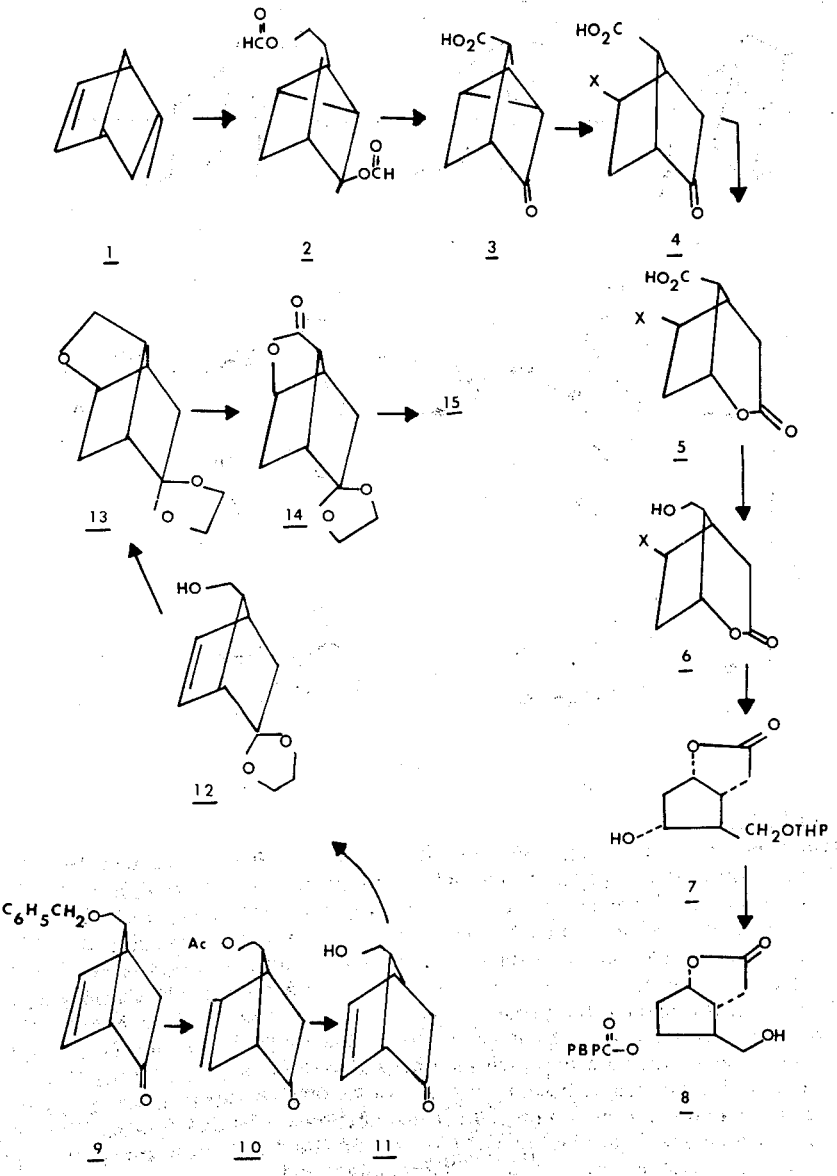

SCHEME II

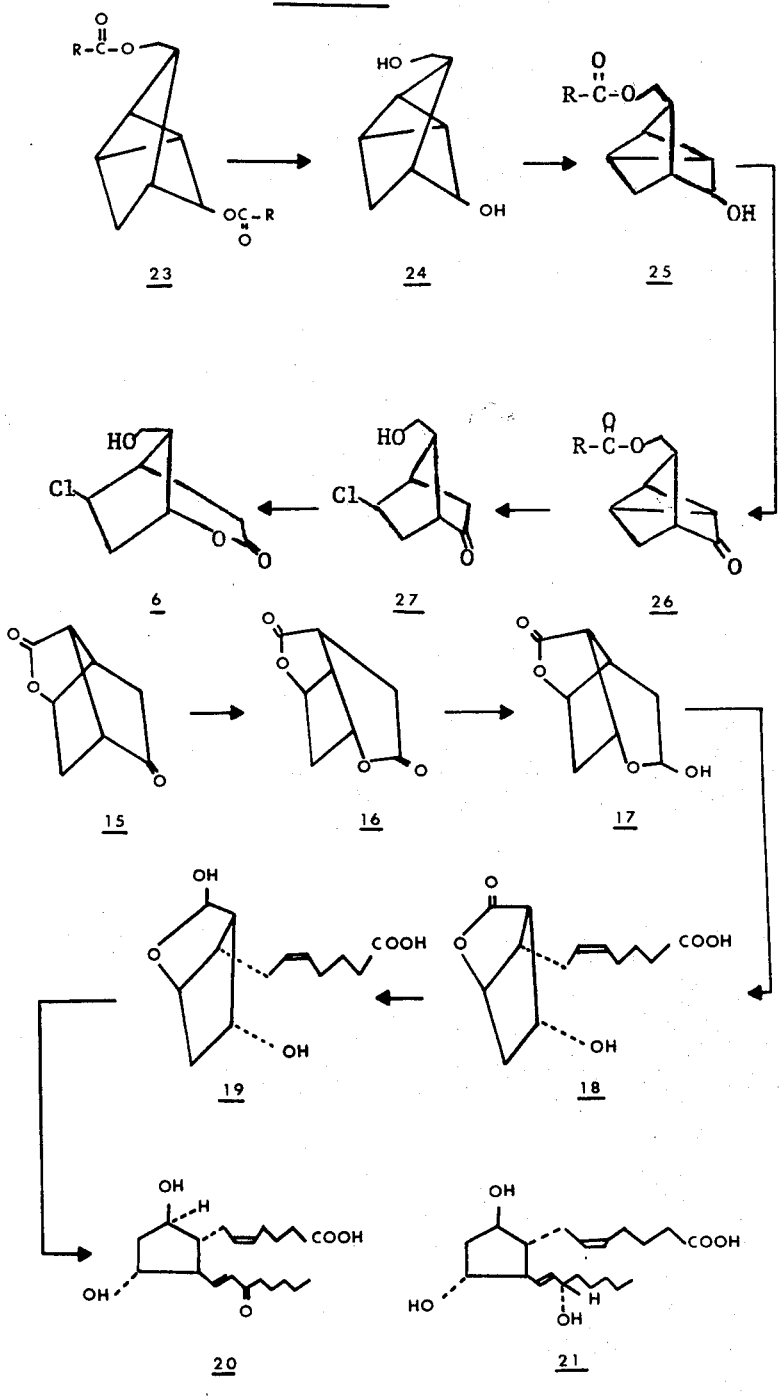

The presence of hydrogen peroxide has been found to be of substantial importance and 30% hydrogen peroxide is preferred. The preferred ratio of hydrogen peroxide to THP ether is about 20:1. The reaction is conveniently conducted at room temperature although temperatures between −5°–50° may be employed. After reaction is complete the product is isolated.

The conversion (7 → 8) is carried out by a simple esterification reaction in which lactone alcohol (7) is dissolved in an organic base, typically pyridine or other tertiary amine, and parabiphenyl carboxylic acid chloride is added and the reaction stirred at room temperature until substantially complete. The reaction mixture is then hydrolyzed with diluted hydrochloric acid at room temperature until the tetrahydropyranyl protecting group has been removed. Extraction of the reaction mixture with a suitable solvent such as ethyl acetate affords the desired key intermediate (8). This intermediate is converted by routes well known in the art to prostaglandins of the A, E and F series and numerous prostaglandin analogs. However, if it is desired to prepare prostaglandins of the Fβ series another intermediate may be prepared which allows the synthesis of these Fβ prostaglandins by a simplified route. This intermediate may be prepared from keto acid (3) in the following way:

Keto acid (3) is contacted with aqueous sulfuric acid at 150° until reaction is substantially complete. The resulting keto lactone (15) is then isolated by solvent extraction. Ethyl acetate is most conveniently employed for this purpose. A wide range of sulfuric acid concentrations may be used, however, 25% aqueous sulfuric acid has been found to be most effective. Other acids may also be used in place of sulfuric acid such as phosphoric or perchloric acids. Temperatures from about 100°–175° are optimum and especially preferred is 150°. The reaction is best run in a sealed vessel to permit achievement of the desired reaction temperature. The product of this reaction can be purified most conveniently by sublimation at 150° and 0.1 mm.

Keto lactone (15) is then oxidized under Bayer-Villiger conditions to dilactone (16). For the purposes of this oxidation, peracetic acid, perbenzoic acid, m-chloroperbenzoic acid or m-nitroperbenzoic acid can be used. M-chloroperbenzoic acid has been found to be most effective. The reaction is run in a reaction inert solvent in the presence of anhydrous sodium carbonate. The solvent for these reactions is most typically methylene chloride although other reaction inert solvents such as carbon tetrachloride may be used. Approximately one equivalent of the oxidizing agent is preferred and similarly one equivalent of anhydrous sodium carbonate has also been found optimum. The reaction may also be run in the absence of sodium carbonate and under these circumstances reduced yields are sometimes obtained. The reaction temperature is maintained from about 25°–40°C by external heating. A temperature of 35° has been found optimum. The product is isolated by first washing the organic layer of aqueous sodium bicarbonate followed by aqueous saturated sodium sulfate solution and subsequently brine. The organic phase is then dried and evaporated to provide dilactone (16).

Dilactone (16) is then reduced to the lactone hemiacetal (17) by use of diisobutyl aluminum hydride. Low temperatures, typically −78°, are employed although any temperature which does not give rise to over reduction of the molecule is satisfactory. The solvent for this reaction is most usually toluene although any reaction inert solvent which is liquid at the reaction temperature may be used. The steps (17 21) are well known in the art of prostaglandin synthesis. (17 18) is a Wittig reaction in which hemiacetel (17) is reacted with 4 carbohydroxy n-butyltriphenylphosphonium bromide in diemthyl sulfoxide in the presence of methylsulfinylmethide. (18 19) is accompanied in the same manner as (16 17) and hemiacetal (19) is reacted with keto phosphonate (23) in the presence of sodium hydride in a reaction inert solvent usually dimethoxyethane to produce keto acid (20). Keto acid (20) is then reduced by methods well known in the art to prostaglandin $F_2$ (21). Zinc borohydride or lithium triethyl borohydride may be used for this purpose and the solvent is most usually dimethoxyethane. Steps (17 21) are similar to those described by E. J. Corey et al., JACS, 92, 2586 (1970); JACS, 93, 1490 (1971); JACS 93, 4327 (1971); and Schaaf and Corey, JOC, 37, 2921 (1972). Keto lactone (15) may also be prepared from the known keto ether (9). (9 10) is accompanied by contacting keto (9) with borotrifluoride etherate in acetic anhydride at a temperature of from about 0°–20°. The resulting acetate (10) is not isolated but hydrolyzed directly with aqueous base, typically sodium or potassium carbonate, to alcohol (11). Alcohol (11) is then ketalized with ethylene glycol to produce ketal (12). Any acid labile ketone protecting group such as hemithioketal or dilower alkyl ketal can be used and the conditions for preparing these ketals or hemithioketals are well known in the art. The ethylene glycol ketal is prepared by refluxing a mixture of keto alcohol (11) in a reaction inert solvent with ethylene glycol and p-toluenesulfonic acid as a catalyst whie azeotropically removing the water formed by the reaction. Benzene is most commonly used as a solvent for this reaction although toluene or other alkyl substituted benzenes may also be used. Other acidic catalysts may also be used such as benzene sulfonic acid, however, p-toluenesulfonic acid is most frequently employed.

Ketal alcohol (12) is then cyclized in a mixture of aqueous mercuric acid and tetrahydrofuran followed by reduction with sodium borohydride. The reduction should be carried out in a strong basic medium and to affect this before the sodium borohydride solution is added the mixture is made basic with sodium hydroxide solution. The reducing agent may be sodium borohydride, potassium borohydride or zinc borohydride, however, sodium borohydride is most commonly employed. The ketal ether (13) is then oxidized with ruthium tetraoxide in carbon tetrachloride. This reaction requires a very large excess of ruthium tetraoxide unless sodium or potassium periodate is present in the reaction mixture for regenerating the ruthium tetraoxide. If sodium or potassium periodate is employed the excess may be reduced to approximately 10 times the weight of ether lactone (13). Lower ratios of ruthium tetraoxide lead to reduced yields and/or longer reaction times. The ketal lactone (14) may then be hydrolyzed with aqueous dilute mineral acid to produce keto lactone (15). This reaction may be facilitated by the addition of inert solvents such as tetrahydrofuran to increase solubility of the reactants. The reaction temperature is not critical and temperatures of from about 25°–50° are most commonly employed.

Compound 6 can also be prepared by a still shorter route from compound 2 or diester 23 wherein R is hydrogen or lower alkyl is hydrolyzed by contacting diester 23 with aqueous mineral base such as alkylene metal carbonate or hydroxide at temperatures from about 0°–100° to produce diol 24. Diol 24 is then converted to mono ester 25 by contacting it with one equivalent of lower alkanoic acid anhydride and a proton acceptor in a reaction inert solvent at a temperature of from about 0°–50° until reaction is substantially complete. The proton acceptor can be organic base such as triethylenediamine or triethylamine and the reaction inert solvent conveniently benzene or if desired, the reaction may be run in pyridine which will serve as a base and a solvent. In such a situation, no additional base is necessary. Mono ester 25 is then oxidized to keto ester 26 by contacting it with about two equivalents of chromium trioxide in reaction inert solvent at a temperature of from about 0°– 25° until reaction is substantially complete. Jones' conditions, that is to say, chromium trioxide, sulfuric acid, acetone are preferred, however, other oxidative means such as chromium trioxide pyridine are also satisfactory. Keto ester 26 is then converted to halo ketone 27 by refluxing with concentrated with 10 to 100 times its weight of concentrated hydrochloric acid at a temperature of from about 100°–150° until reaction is substantially complete. The order of the last two steps may be inverted by first oxidizing keto ester 26 to a lactone ester which is then refluxed with the desired halo acid to provide compound 6. The bromo ketone can be obtained in a similar way by substituting hydrobromic acid for hydrochloric acid in the above reaction. Compound 27 is then converted to compound 6 by means of Bayer-Villiger oxidation in the manner described for the conversion of (4 5) in the synthesis described above.

A special advantage of the synthetic sequences of this invention is that for the intermediate products are easy to isolate and purify. In most of the sequences no chromatography is required. Furthermore, the novel synthetic sequences of the present invention require very simple and inexpensive starting materials and are readily adaptable to large scale preparations.

In the synthesis described above where ketals are used as ketone protecting groups the obvious equivalents of ethylene glycol ketals such as hemithioketals or a dilower alkyl ketals will be clear to those skilled in the art. Likewise, in other reaction steps described herein such as oxidation of alcohols to ketals the reaction conditions are not critical and a wide variety of known techniques will occur to those skilled in the art.

The invention claimed is not limited to the specific conditions cited in the examples to follow. Melting points and boiling points are given in degree of Centigrade. All melting and boiling points are uncorrected. Infrared data is given in microns, MNR is given in parts per million using TMS as a standard. The following examples are merely illustrative and in no way limit the scope of the appended claims.

EXAMPLE I

3-Hydroxymethyl tricyclo [2.2.1.0$^{2,6}$/heptan-5-ol bisformate (1′)

To a stirred solution of 39.9 g paraformaldehyde in formic acid (800 ml) and conc. $H_2SO_4$ (15 ml) under nitrogen and at 20°C was added dropwise 132 g norbornadiene while keeping the temperature between 20°–25°C. After 1.5 hr the reaction was quenched by adding to 800 ml of ice-water. Extraction with ether (3 × 750 ml), washing the organic layer with water (1 × 250 ml), brine (3 × 250 ml) and drying ($Na_2SO_4$) afforded the crude 3-hydroymethyl tricyclo [2.2.1.0$^{2,6}$]heptan-5-ol bisformate (1′) as an oil. Distillation, after a forerum of bp. 40°C/15mm, gave 235 g pure tricyclenebisformate, bp. 104°C/0.3 mm (84% yield).

IR, 5.81 and 8.55 $\mu$ ($CHCl_3$)

NMR, 8.1 (singlet, 2H), 4.8 (1H), 4.1 (triplet, 2H) δ.

EXAMPLE II 3-carboxy tricyclo [2.2.1.0$^{2,6}$]heptan-5-one (2′)

To a cooled solution of 58.8 g tricyclene bisformate (1′) in acetone (1,200 ml) at 0°C with vigorous stirring was added 2.67 M Jones reagent (370 ml) over a period of 10 min, maintaining the temperature below 5°C. After stirring overnight, the reaction was quenched by addition of isopropanol (20 ml) followed by addition of solid NaCl (500 g). The reaction mixture was filtered, solids washed with ethylacetate, and the combined filtrate after evaporation afforded the crude 3-carboxy tricyclo [2.2.1.0$^{2,6}$] heptan-5-one (2′). Crystallization from ethyl acetate gave colorless crystals, m.p. 144°–145°C, of pure tricyclene ketoacid (34 g, 72% yield).

IR, 5.68 and 5.85 $\mu$ ($CHCL_3$)

NMR, 9.5 (1H, exchangeable), 3.1 (singlet, 1H), 2.35 (multiplet, 3H), 2.0 (singlet, 2H), 1.55 triplet, 1H) δ.

Optically active material had m.p. 138°, $[\alpha]_D^{25}$ + 74° (C 1.0 MeOH)

EXAMPLE III

Lactone of 5-hydroxy-2-oxo-bicyclo[2.2.1]heptan-7-oic acid (3)

A solution of the ketoacid (2) (182 mg) in 25% aq. $H_2SO_4$ was refluxed (bath temperature, 150°C) for 12 hr. The cooled mixture was treated with solid sodium chloride, and extracted with ethyl acetate. The organic layer was washed with saturated $NaHCO_3$, brine, dried ($Na_2SO_4$) and concentrated. Sublimation of the crude product at 150°C/0.1 mm afforded 132 mg (70% yield) of lactone of 5-hydroxy-2-oxo-bicyclo[2.2.1]heptan-7-oic acid (3), m.p. 195°–96°C.

IR, 5.59, 5.69, 10.20 and 10.52 $\mu$ ($CHCl_3$)

NMR, 4.9 (1H), 3.3 (1H), 3.15–2.6 (2H), 2.3 (2H), 2.2–1.9 (2H) δ

Optically active material had m.p. 196°–97°C, $[\alpha]_D^{25}$ + 270°.

EXAMPLE IV (2β-carboxyl-3α,5β-dihydroxy-cyclopent-1α-yl)acetic acid, γ, δ-lactone (4′).

To a stirred mixture of 196 mg ketolactone (3′), 328 mg anhydrous $Na_2CO_3$ in methylene chloride (10 ml) was added 276 mg m-chloroperbenzoic acid over a period of 1.5 hr and temperature maintained at 35°C by external heating. After 4 hr the reaction mixture was cooled, filtered and the organic layer washed with saturated $NaHCO_3$ (1 × 5 ml), saturated $Na_2SO_4$ (1 × 5 ml), brine (1 × 5 ml), dried ($Na_2SO_4$) and evaporated to give 150 mg of pure (2β-carboxyl-3α,5β-dihydroxy-cyclopent-1α-yl)acetic acid, δ, δ-lactone (4′).

IR, 5.57 and 5.71 $\mu$ ($CHCl_3$)

Mass spectrum, M+ at 168.

EXAMPLE V

5-Chloro-2-oxo-bicyclo[2.2.1]heptan-7-oic acid (5′)

A continuous stream of HCl gas was passed into a refluxing solution of 5.0 g of the ketoacid (2′) in water (250 ml) for 4 hr. The reaction mixture was evaporated to dryness under reduced pressure and the residue crystallized from ether to give pure 5-chloro-2-oxo-bicyclo[2.2.1]heptan-7-oic acid (5′).

Optically active material had m.p. 156°, $[\alpha]_D^{25}$ + 14° (C. 1.0 MeOH).

EXAMPLE VI (2β-Carboxy-3α-hydroxy-5β-chlorocyclopent-1α-yl)acetic acid, δ-lactone (6′).

A mixture of 188 mg chloro ketoacid (5′), 0.265 g 40% peracetic acid, 117 mg $NaHCO_3$ in methylene chloride (10 ml) was stirred and heated at 35°C for 5 hr. The reaction mixture was cooled, filtered and evaporated to dryness. Crystallization of the residue from ether afforded 140 mg (70% yield) of (2β-carboxy-3α- hydroxy-5β-chlorocyclopent-1α-yl)acetic acid, δ-lactone (6'), m.p. 180°–81°C.

Optically active material had mp 166°, [α]$_D^{25}$ −70° (C. 1.0 MeOH).

EXAMPLE VII

2[2β-tetrahydropyran-2-yloxymethyl-3α-hydroxy)-5α-hydroxycyclopent-1α-yl]acetic acid, γ-lactone (8')

To a solution of chloro alcohol (7') (229 mg) in methylene chloride (10 ml) was added dihydropyran (0.32 ml) and a catalytic amount of p-toluenesulfonic acid. After 1 hr the reaction mixture was washed with brine, dried ($Na_2SO_4$) and evaporated to a colorless oil. The crude THP-ether thus obtained was dissolved in THF (6.5 ml) and heated with 30% $H_2O_2$ (3.3 ml) followed by a solution of LiOH (29 mg) in water (3.3 ml). The solution was stirred 1 hr at room temperature, diluted with ethyl acetate (35 ml) and washed with saturated $Na_2SO_3$ (10 ml). After drying ($Na_2SO_4$) evaporation afforded 260 mg of the desired 2[2β-tetrahydropyran-2-yloxymethyl-3α-hydroxyl)-5α-hydroxycyclopent-1α-yl]acetic acid, γ-lactone (8'). IR, 1770 cm$^{-1}$ ($CHCl_3$).

EXAMPLE VIII

2[2β-hydroxymethyl-3α-p-phenylbenzoyloxy-5α-hydroxy cyclopentan-1α-yl]acetic acid, γ-lactone.

To a solution of the γ-lactone (8') (44 mg) in pyridine (0.27 ml) was added p-biphenylcarboxylic acid chloride (46 mg) and the mixture stirred overnight. The reaction was quenched by adding a little methanol, and stirred with dilute HCl (2 ml) for 6 hrs to remove the THP group. Extraction with ethyl acetate afforded 32 mg of the desired 2[2β-hydroxymethyl-3α-p-phenylbenzoyloxy-5α-hydroxy cyclopentan-1α-yl]acetic acid, γ-lactone, mp 130°–31°, [α]$_D^{25}$ = −86.5° (C 1.0 $CHCl_3$).

EXAMPLE IX (2β-Hydroxymethyl-3α-hydroxy-5β-chlorocyclopent-1α-yl)acetic acid, δ-lactone (7').

To a solution of chloro acid lactone (6') (1.43 g, 7 mmole) in 28 ml tetrahydrofuran cooled to 0° and under nitrogen, was added 0.756 g (7 mmole) of ethyl chloro formate followed by dropwise addition of a solution of 0.70 g (7 mmole) triethylamine in 14 ml tetrahydrofuran. A precipitate formed immediately and the cold mixture stirred for 10 min. The reaction mixture was filtered under a nitrogen cover and the filtrate kept at 0°. The filtered solid was washed with cold tetrahydrofuran (2 × 5 ml). The combined filtrate was stirred at 0° and 5.2 ml. (5.2 mmole) of a 1M solution of zinc borohydride in DME was added dropwise. The reaction mixture was quenched with saturated sodium bitartrate, diluted with 50 ml methylene chloride and dried over sodium sulfate. Filtration and evaporation gave the crude chloro lactone alcohol (1.46 g yield 100%) which was purified by column chromatography, to give 1.2 g of pure (2β-hydroxymethyl-3α-hydroxy-5β-chlorocyclopent-1α-yl)acetic acid, δ-lactone.

IR: 1735 cm$^{-1}$
NMR: 4.95 (1H, M), 4.30 (1H, double doublet), 3.90 (2H, doublet, 7.0 cps) δ
Optically active material had mp 130°, [α]$_D^{25}$ −65° (C 1.0, $CHCl_3$).

EXAMPLE X 7-hydroxymethyl bicyclo [2.2.1]hept-2-ene-6-one acetate (10').

A cooled (0°C), stirred solution of 4.99 g 7-hydroxymethyl bicyclo [2.2.1]hept-2-ene-6-one benzyl ether in acetic anhydride (109 ml) was treated with $BF_3$-etherate (0.63 ml). After 15 min, the reaction was quenched by addition of water (19 ml) and the mixture evaporated in vacuo to dryness, affording 3.9 g oily 7-hydroxymethyl bicyclo [2.2.1]hept-2-ene-6-one acetate (10').

IR, 5.73 μ ($CHCl_3$).
NMR, 6.50 (9, 1H), 6.0 (1H), 4.15 (d, J = 7 cps, 2H), 2.05 (S, 3H)δ.

EXAMPLE XI 7-hydroxymethyl bicyclo[2.2.1]hept-2-ene-6-one (11')

Powdered, dry $K_2CO_3$(1.51 g) was added to stirred solution of the ketoacetate (10') (1.96 g) in methanol (45 ml) at room temperature. After 20 min, 6N HCl (3.6 ml) was added and the mixture evaporated to dryness. The residue was extracted with ethyl acetate to give 1.0 g of 7-hydroxymethyl bicyclo[2.2.1]hept-2-ene-6-one (11') homogenous on tlc (Rf 0.25, $C_6H_6$:MeOH, 17:3).

IR, 5.74 μ ($CHCl_3$).

EXAMPLE XII 7-hydroxymethyl bicyclo[2.2.1]hept-2-ene-6-one ketal (12')

A mixture of ketoalcohol (11') (1.05 g), ethylene glycol (0.98 g) and p-toluene sulfonic acid (0.16 g) in benzene (250 ml) was refluxed 16 hr, while water was removed azeotropically. The cooled solution was washed with saturated $NaHCO_3$ (1 × 10 ml), brine (1 × 10 ml), dried ($Na_2SO_4$) and evaporated to the oily 7-hydroxymethyl bicyclo[2.2.1]hept-2-ene-6-one (12') ketal, 1.1 g.

IR, 2.75-3.15 (OH) μ (neat)
NMR, 5.80–6.30 (2H), 3.95 (singlet, 4H), 3.55 (d, J = 7.0, 2H), 2.0 (dd, J = 13.5 & 3.5, 1H), 1.55 (d, J = 13.5, 1H) δ.

EXAMPLE XIII 6-oxo-9-oxatricyclo[4.3.0.0$^{3,7}$]nonane ketal (13')

To a stirred yellow mixture of 4.0 g Hg (OAc)$_2$ in $H_2O$-THF (1:1) (12.6 ml) was added 1.15 g ketal alcohol (12') dissolved in THF (1.5 ml). The yellow color disappeared within 5 min, and 3 M NaOH (6.3 ml) was added to the reaction mixture followed by 6.3 ml of 0.5 ml $NaBH_4$ solution in 3 M NaOH. The precipitated mercury was filtered off, solid NaCl added to the filtrate and extracted with ethyl acetate. Concentration of organic extracts afforded 720 mg of oily 6-oxo-9-oxatricyclo[4.3.00$^{3,7}$]nonane ketal (13') homogenous on tlc (Rf 0.52, CH Cl :MeOH, 19:1).

NMR, 4.2 (1H), 4.1–3.6 (6H), 2.8–1.2 (7H) δ.

EXAMPLE XIV 2-hydroxy-5-oxo-bicyclo[2.2.1]heptan-7-oic acid ketal (14)

A mixture of 0.58 g ether ketal (13) in 3% $RuO_4$ solution in $CCl_4$ (2 ml) and 10 ml of saturated aqueous NaIO$_4$ was stirred 18 hr at room temperature. The black precipitate was filtered off, and the organic layer separated, dried (Na$_2$SO$_4$), gave 47 mg of 2-hydroxy-5-oxo-bicyclo[2.2.1]heptan-7-oic acid (14) ketal as an oil, homogenous on tlc (Rf 0.45, C$_6$H$_6$:EtOAC, 3:1).

IR, 5.63 $\mu$ (CHCl$_3$)

Treatment with acid afforded the ketolactone (3).

EXAMPLE XV

3-Hydroxymethyltricyclo [2.2.1.0$^{2,6}$]heptan-5-ol (15')

To a stirred refluxing solution of 5 g of tricyclene bisformate (1') in methanol (20 ml) is added 0.5 g of sodium methoxide and the resulting methylformate distilled off. After completion of reaction CO$_2$ is bubbled into the reaction mixture, solids are filtered off and solvent evaporated to dryness to give 3-hydroxymethyltricyclo [2.2.1.0$^{2,6}$]heptan-5-ol (15').

EXAMPLE XVI

3-Acetoxymethyltricyclo [2.2.1.0$^{2,6}$]heptan-5-ol (16')

To a stirred solution of 14 gm of the diol (15') in 100 ml pyridine is added acetic acid. The reaction is stirred overnight at 25° and quenched by addition of ice-water. The product is extracted with CH$_2$Cl$_2$. The CH$_2$Cl$_2$ layer washed with dil. HCl, dried (Na$_2$SO$_4$) and concentrated to give 3-acetoxymethyltricyclo [2.2.1.0$^{2,6}$]heptan-5-ol (16').

EXAMPLE XVII

3-Acetoxymethyltricyclo [2.2.1.0$^{2,6}$]heptan-5-one (17')

To a cooled solution of 6 gm acetoxy alcohol (16') in 150 ml acetone at 0°C with vigorous stirring is added 2.67 M Jones reagent (40 ml) over a period of 10 min. After stirring 5 hr, the reaction is quenched by addition of isopropanol (2 ml) followed by dilution with water. Extraction with CH$_2$Cl$_2$ affords the title product.

EXAMPLE XVIII

2-Acetoxymethyl-3-hydroxy-bicyclo [3.1.0]hexan-6-oic acid lactone (18')

To a stirred mixture of 2 g of acetoxy ketone (17') in methylene chloride (100 ml) is added 2.8 g m-chloroperbenzoic acid and the solution refluxed for 6 hr. The reaction mixture is cooled, filtered and the organic layer washed with saturated NaHCO$_3$, saturated Na$_2$SO$_4$, brine, dried (Na$_2$SO$_4$) and evaporated to give 2-acetoxymethyl-3-hydroxy-bicyclo [3.1.0]hexan-6-oic acid lactone (18').

EXAMPLE XIX

2$\beta$-Hydroxymethyl-3$\alpha$-hydroxy-4$\beta$-chloro-cyclopent-1$\alpha$-yl)acetic acid $\delta$-lactone (7')

A mixture of 2 g acetoxy lactone (18') and concentrated HCl (20 ml) is refluxed for 4 hr. The reaction mixture is evaporated to dryness under reduced pressure and the residue crystallized from ether to give pure 2$\beta$-hydroxymethyl-3$\alpha$-hydroxy-4$\beta$-chlorocyclopent-1$\alpha$-yl)acetic acid, $\delta$-lactone (7').

What is claimed is:

1. A compound of the structure:

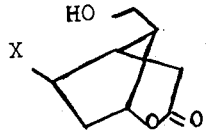

wherein X is chlorine, bromine or iodine.

2. The compound of claim 1 wherein X is chlorine.
3. The compound of claim 1 wherein X is bromine.